US00PP22766P3

(12) United States Plant Patent
Decourtye

(10) Patent No.: US PP22,766 P3
(45) Date of Patent: Jun. 5, 2012

(54) ***WEIGELA* PLANT NAMED 'COURTACAD1'**

(50) Latin Name: ***Weigela* hybrid**
Varietal Denomination: Courtacad1

(76) Inventor: Luc Decourtye, Moltig des Bains (FR)

( * ) Notice: Subject to any disclaimer, the term of this patent is extended or adjusted under 35 U.S.C. 154(b) by 0 days.

(21) Appl. No.: 12/925,013

(22) Filed: Oct. 12, 2010

(65) Prior Publication Data

US 2012/0090059 P1 Apr. 12, 2012

(51) Int. Cl.
*A01H 5/00* (2006.01)

(52) U.S. Cl. ..... Plt./226

(58) Field of Classification Search ..... Plt./226
See application file for complete search history.

*Primary Examiner* — Kent L Bell
(74) *Attorney, Agent, or Firm* — Cassandra Bright

(57) ABSTRACT

A new and distinct *Weigela* cultivar named 'COURTACAD1' is disclosed, characterized by bronze foliage, white flowers and a weeping, compact habit. The new variety is a *Weigela,* normally produced as an outdoor ornamental plant for containers or gardens.

2 Drawing Sheets

Figure 1:
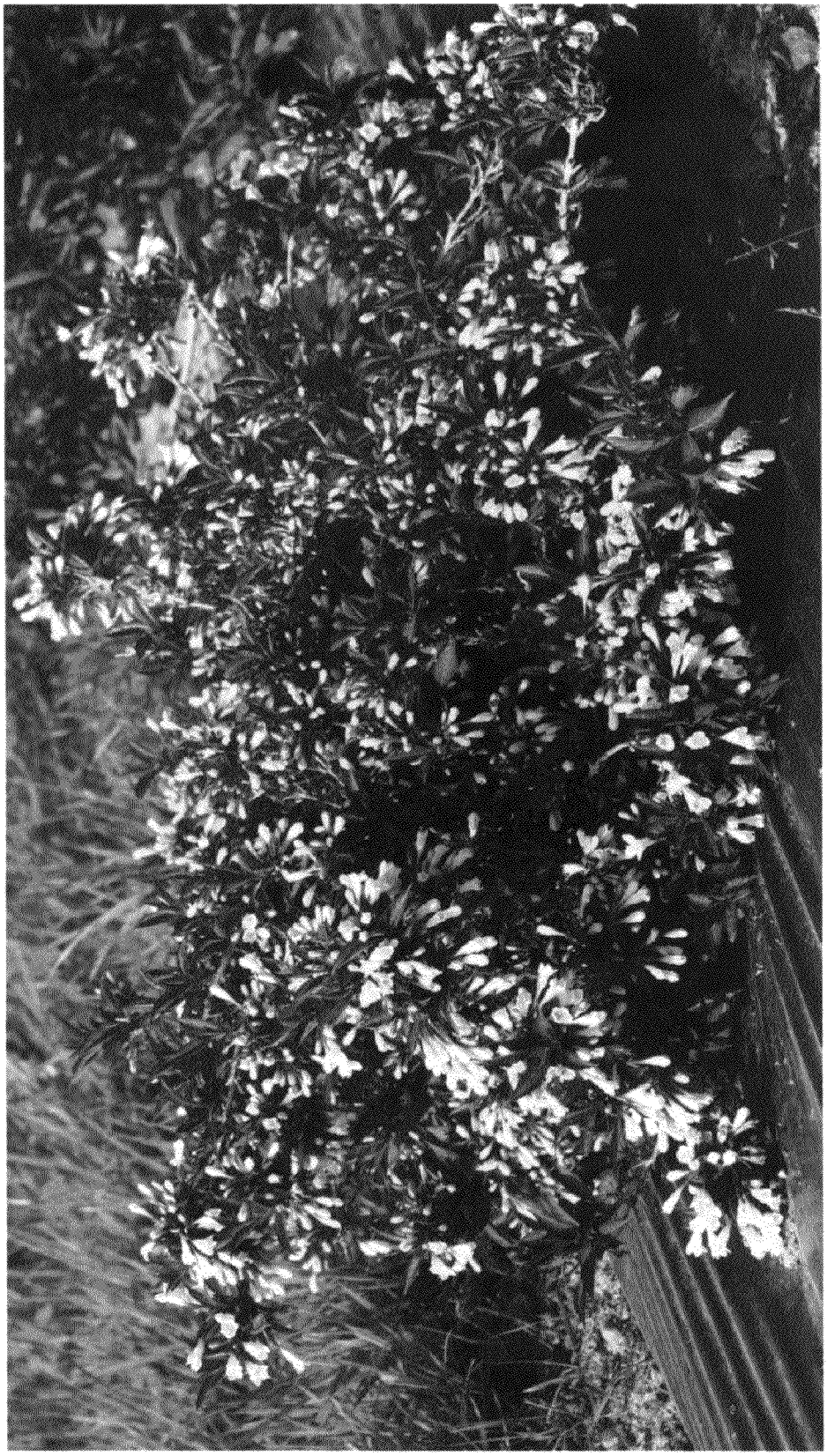

Latin name of the genus and species: *Weigela* hybrid.
Variety denomination: 'COURTACAD1'.

BACKGROUND OF THE INVENTION

The new cultivar was discovered as a result of a planned breeding program directed by the inventor, Luc Decourtye, a citizen of France. 'Courtacad1' is a selection from a planned breeding program. First the breeder conducted a cross-pollination of *Weigela* hybrid 'Mansais' (unpatented) as the female parent, and *Weigela florida* 'Foliis Purpureis' (unpatented) as the male parent. This initial cross-pollination of the parent plants took place in Beaucouzé, France in 1987. Subsequently, the F1 generation resulting from the 1987 cross was self-pollinated and seed collected and planted during the following year. From these F2 seedlings a selection was made of the seedling now referred to as 'Courtacad1' in 1989, by the inventor in a research nursery in Beaucouzé, France. The exact seed and pollen parents are unknown.

Asexual reproduction of the new cultivar 'COURTACAD1' was first accomplished in 2006 by vegetative cuttings at a research nursery in Angers, France. Multiple generations have since been produced and have shown that the unique features of this cultivar are stable and reproduced true to type in successive generations.

SUMMARY OF THE INVENTION

The cultivar 'COURTACAD1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COURTACAD1' These characteristics in combination distinguish 'COURTACAD1' as a new and distinct *Weigela* cultivar:

1. Bronze colored foliage.
2. White flowers
3. Compact, weeping plant habit.
4. Early flowering

COMMERCIAL COMPARISON

Plants of the new cultivar 'COURTACAD1' are similar to plants of *Weigela* hybrid 'Mansais' in most horticultural characteristics, however, plants of the new cultivar 'COURTACAD1' have smaller flowers, and bronze colored foliage, whereas plants of 'Mansais' have green foliage.

Plants of the new cultivar 'COURTACAD1' are similar to plants of the *Weigela florida* 'Foliis Purpureis' in most horticultural characteristics, however, plants of the new cultivar 'COURTACAD1' white flowers whereas plants of 'Foliis Purpureis' have pink/purple flowers. Additionally the flower shape of the two varieties is different and the foliage color of 'COURTACARD1' has bronze coloration, whereas 'Foliis Purpureis' has foliage with a combination of dark purple with green.

'COURTACAD1' can be compared to the commercial variety *Weigela forida* 'Verweig' U.S. Plant Pat. No. 16,824. The two varieties are similar in many horticultural characteristics, however, plants of 'COURTACAD1' differ in producing different colored foliage, and different colored flowers.

'COURTACAD1' can also be compared to the commercial variety *Weigela forida* 'Alexandra' U.S. Plant Pat. No. 10,772. The two varieties are similar in many horticultural characteristics, however, plants of 'COURTACAD1' differ in producing different colored foliage, and different colored flowers.

BRIEF DESCRIPTION OF THE PHOTOGRAPH

The accompanying photograph in FIG. 1 illustrates in full color a typical plant of 'COURTACAD1' grown outdoors in Angers, France , in a 10 liter nursery container.

Figure 2:
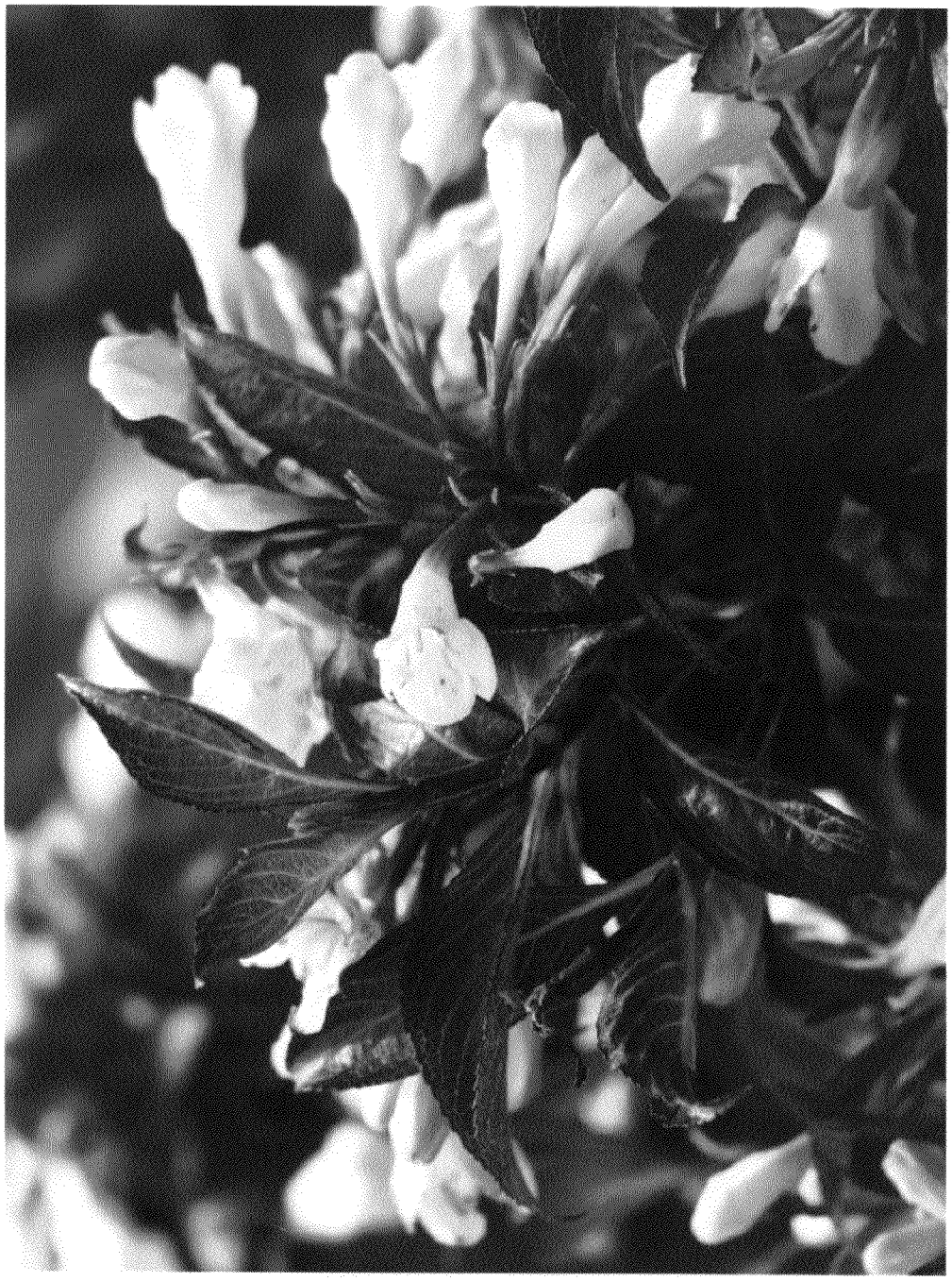

FIG. 2. shows a close up of the flower and foliage, specifically illustrating the bronze coloration of the young foliage. Age of the plant photographed is approximately 36 months from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'COURTACAD1' plants grown outdoors in a research nursery in Angers, France. The growing temperature ranged from 10° C. to 35° C. daytime and 10° to 20° C. at night. No growth regulators or other chemical treatments were used. Measurements and numerical values represent averages of typical plant types.

Botanical classification: *Weigela* hybrid 'COURTACAD1'

PROPAGATION

Time to initiate roots: About 30 to 45 days at approximately 20-25 ° C.
Root description: Fibrous
Root color: Near RHS Orange-White 159C.
Propagation method: Vegetative semi-woody cuttings

PLANT

Age of plant described: Approximately 36 months from a rooted cutting
Growth habit: Weeping, compact
Pot size of plant described: 10 liter
Height: 25 to 30 cm.
Plant spread: 30 to 35 cm.
Growth rate: Moderate
Branching characteristics: Shrub
Length of primary lateral branches: 25 to 30 cm.
Diameter of lateral branches: 0.2 to 0.3 cm.
Quantity of primary lateral branches: 8 to 12
Characteristics of primary lateral branches:
- *Form.*—Cylindrical with two opposite ribs
- *Diameter.*—0.4 to 0.6 cm.
- *Color.*—Young: near Greyed-Purple 183A mature near Grey-Brown N199C.
- *Texture.*—Rough and pulverulent.
- *Strength.*—Moderate.

Internode length: 1 to 2 cm

FOLIAGE

Leaf: Winter deciduous
- *Arrangement.*—Opposite with a 180° angle between two nodes.
- *Quantity.*—Approximately 26 to 34 per branch on primary lateral.
- *Average length.*—5 cm.
- *Average width.*—2 cm.
- *Shape of blade.*—Kanceolate to acuminate.
- *Apex.*—Acuminate.
- *Base.*—Attenuate.
- *Margin.*—Crenulate.
- *Texture of top surface.*—Smooth.
- *Pubescence.*—No.
- *Aspect.*—Slight upcurve from main vein.
- *Color.*—Leaf colors can be slowly modified and change according to temperature, soil conditions and season. The following data represents plants during May to August, grown in artificial potting soil, outdoors in Angers France. Young foliage upper side: Near RHS Brown 200 A, B and C, all colors present, tinged with RHS Yellow-Green N147B. Young foliage under side: Near RHS Brown 200C. Mature foliage upper side: Near RHS Yellow-Green N137B. Mature foliage under side: Near RHS Yellow-Green 147B.
- *Venation.*—Type: Pinnate. Venation color upper side: Near RHS Yellow-Green 145B. Venation color under side: Near RHS Yellow-Green 145B.
- *Petiole.*—Flattened sub-cylindrical. Length: Near 0.5 cm. Diameter: Near 0.2 cm. Color: Near RHS Yellow-Green 145 B with Greyed-Purple 183 B along the upper margin. Texture: villous.

FLOWER

Flowering season: Continutously flowering from Spring through early summer
Days to flowering from rooted cutting: About 20 months
Inflorescence and flower type and habit: Funnelform flowers in corymb
Flower longevity on plant: Approximately 7 weeks
Approximate quantity of flowers per plant: About 400 on a 3 year old plant. Average 10 to 15 flowers per corymb.
Persistent or self-cleaning: Self cleaning
Bud:
- *Shape.*—Tubular.
- *Length.*—1 to 1.5 cm.
- *Diameter.*—0.1 to 0.2 cm.
- *Color.*—Near RHS Yellow-Green 154 D.

Flower size: Corolla shape: funnel
- *Diameter.*—Base: 0.1 cm and 0.7 to 1 cm at apex.
- *Length.*—3 to 3.5 cm.
- *Flower tube diameter at distal end.*—Approximately 0.5 to 0.7 cm.
- *Flower tube diameter at proximal end.*—Approximately 0.1 cm.

Petals: Lobes
- *Length.*—2 to 2.5 cm.
- *Width.*—2 to 2.5 cm.
- *Shape.*—Spatulate.
- *Quantity.*—5.
- *Texture.*—Smooth.
- *Apex.*—Rounded.
- *Margin.*—Entire.

Color:
- *When opening.*—Inner surface: Near RHS White N 155 D. Outer surface: Near RHS White N 155 D.
- *Fully opened.*—Inner surface: Near RHS White N 155 B. Outer surface: Near RHS White N 155 D. Flower throat (inside): Near RHS Red-Purple 69 B. Flower throat, vein: Near RHS Red-Purple 60 C. Flower tube (outside): Near RHS Red-Purple 62 C. Flower tube, vein: Near RHS Red-Purple 59 B. Petal color, fading to: Not fading.

Calyx/sepals:
- *Quantity per flower.*—5 sepals.
- *Shape.*—Fused, tubular on lower ⅔ and campanulate on top.
- *Length.*—1.3 to 1.5 cm.
- *Width.*—0.1 cm.
- *Apex.*—Acuminate.
- *Base.*—Fused, tubular.
- *Margin.*—Entire.
- *Texture.*—Smooth.
- *Color.*—Upper Surface: Near RHS Greyed-Yellow 160C with a strong flush of 59B.

*Lower surface.*—Near RHS Greyed-Yellow 160C with a strong flush of 59B.

Pedicel:

*Length.*—0.1 to 0.5 cm.

*Diameter.*—0.1 cm.

*Color.*—Near RHS N 186C.

*Texture.*—Smooth.

*Orientation.*—Upright.

Peduncle:

*Length.*—5 to 15 cm.

*Diameter.*—Approximately 0.8 to 1 cm.

*Color.*—Near RHS Greyed-Purple 183B.

*Texture.*—Smooth.

*Orientation.*—Straight, approximately 15° to 45° angle from stem.

Fragrance: None observed

REPRODUCTIVE ORGANS

Androecium:

*Stamens.*—Number: 5. Filament length: 2 cm.

*Anthers.*—Length: 0.2 to 0.3 cm. Shape: linear, with hook at upper end. Color: 166 B to 166 C RHS both colors present. Pollen: Color: Near RHS Greyed-Orange 166 C. Quantity: moderate.

*Pistil.*—Number: 1. Length: 2.2 to 2.5 cm. Style: Length: 2.1 to 2.4 cm. Color: Near RHS Red-Purple 60C on base and 69B on top. Stigma: Shape: ovoid. Color: Near Yellow-White 158 B. Ovary: Color: Near RHS Red-Purple 69C. Diameter: Approximately 0.8 cm.

OTHER CHARACTERISTICS

Seeds and fruits: Small amount of seed observed to date. Round, approximately 0.5 cm, near RHS Brown 200B. Not germinated to date, fertility undetermined to date.

Disease/pest resistance: Neither resistance nor susceptibility to pathogens and pests common to *Weigela* have been observed.

Temperature tolerance: The new variety has been observed to tolerate temperatures to at least as low as −20 ° C. and above 35° C.

What is claimed is:

1. A new and distinct cultivar of *Weigela* plant named 'COURTACAD1' as herein illustrated and described.

* * * * *